United States Patent
Jiang et al.

(10) Patent No.: US 11,827,933 B2
(45) Date of Patent: Nov. 28, 2023

(54) BUBBLE-SHAPED ADAPTOR ELEMENT AND METHOD OF CONSTRUCTING SEQUENCING LIBRARY WITH BUBBLE-SHAPED ADAPTOR ELEMENT

(71) Applicant: MGI TECH CO., LTD., Shenzhen (CN)

(72) Inventors: Yuan Jiang, Shenzhen (CN); Xia Zhao, Shenzhen (CN); Qiaoling Li, Shenzhen (CN); Shengmao Liu, Shenzhen (CN); Bo Wang, Shenzhen (CN); Li Chen, Shenzhen (CN); Wenwei Zhang, Shenzhen (CN); Hui Jiang, Shenzhen (CN); Radoje Drmanac, Los Altos Hill, CA (US)

(73) Assignee: MGI TECH CO., LTD., Shenzhen (CN)

( * ) Notice: Subject to any disclaimer, the term of this patent is extended or adjusted under 35 U.S.C. 154(b) by 312 days.

(21) Appl. No.: 17/172,927

(22) Filed: Feb. 10, 2021

(65) Prior Publication Data
US 2021/0164042 A1    Jun. 3, 2021

Related U.S. Application Data

(63) Continuation of application No. 15/528,362, filed as application No. PCT/CN2014/091952 on Nov. 21, 2014, now Pat. No. 10,954,559.

(51) Int. Cl.
*C12Q 1/6874*    (2018.01)
*C12Q 1/68*    (2018.01)
(Continued)

(52) U.S. Cl.
CPC ............ *C12Q 1/6874* (2013.01); *C12Q 1/68* (2013.01); *C12Q 1/6855* (2013.01); *C12Q 1/6869* (2013.01)

(58) Field of Classification Search
CPC ................ C12Q 1/6855; C12Q 1/6869; C12Q 2525/191
See application file for complete search history.

(56) References Cited

U.S. PATENT DOCUMENTS

| 4,935,357 A | 6/1990 | Szybalski |
| 10,316,356 B1 | 6/2019 | Jiang et al. |

(Continued)

FOREIGN PATENT DOCUMENTS

| CN | 101466847 A | 6/2009 |
| CN | 102181943 A | 9/2011 |

(Continued)

OTHER PUBLICATIONS

International Search Report issued for PCT/CN2014/091952, dated Aug. 26, 2015.
(Continued)

*Primary Examiner* — Teresa E Strzelecka
(74) *Attorney, Agent, or Firm* — Westman, Champlin & Koehler, P.A.; Z. Peter Sawicki; Amanda M. Prose

(57) ABSTRACT

Provided are an adaptor element in a bubble shape, a method of constructing a sequencing library with such an adapter element. The adaptor element is a hybrid formed with a long-chain nucleic acid A and a short-chain nucleic acid B. The hybrid is in the bubble shape with paired regions at two terminals and a non-paired region in the middle.

20 Claims, 4 Drawing Sheets

Specification includes a Sequence Listing.

(51) Int. Cl.
*C12Q 1/6869* (2018.01)
*C12Q 1/6855* (2018.01)

(56) References Cited

U.S. PATENT DOCUMENTS

| | | | |
|---|---|---|---|
| 10,479,991 | B2 | 11/2019 | Jiang et al. |
| 2007/0172839 | A1 | 7/2007 | Smith et al. |
| 2008/0287320 | A1 | 11/2008 | Baynes et al. |
| 2012/0015823 | A1 | 1/2012 | Bignell et al. |
| 2012/0122161 | A1 | 5/2012 | Musgrave-Brown et al. |
| 2012/0135893 | A1 | 5/2012 | Drmanac et al. |
| 2013/0052639 | A1 | 2/2013 | Seo et al. |
| 2013/0157870 | A1 | 6/2013 | Pushkarev et al. |
| 2014/0024536 | A1 | 1/2014 | Richards et al. |
| 2015/0265995 | A1 | 9/2015 | Head et al. |
| 2016/0046986 | A1 | 2/2016 | Eltoukhy et al. |
| 2017/0211140 | A1 | 7/2017 | Schmitt et al. |

FOREIGN PATENT DOCUMENTS

| | | |
|---|---|---|
| CN | 102296065 A | 12/2011 |
| CN | 102978205 A | 3/2013 |
| CN | 103667273 A | 3/2014 |
| WO | 0206500 A2 | 1/2002 |
| WO | 2011112718 A1 | 9/2011 |

OTHER PUBLICATIONS

Written Opinion of the International Searching Authority issued for PCT/CN2014/091952, dated Aug. 26, 2015.
Office Action issued in Chinese application No. 201480083528.8 dated Jan. 14, 2020.
James Schiemer (Tufts University Core Facility, Illumina TruSeq DNA Adapters De-Mystified, pp. 1-5, retrieved on Jul. 20, 2018 from http://tucf-genomics.tufts.edu/documents/protocols) (Year: 2011).
NEBuffer Activity Chart for restriction enzymes, New England Biolabs, pp. 1-7, on the line, retrieved from New England Biolabs Inc., on Sep. 16, 2019, http://www.neb.com/nebcomm/tech_reference/restriction-enzymes/buffer_activity_restriction_enzymes.asp (Year: 2005).

SEQUENCE LISTING

```
<160> NUMBER OF SEQ ID NOS: 9

<210> SEQ ID NO 1
<211> LENGTH: 45
<212> TYPE: DNA
<213> ORGANISM: Artificial Sequence
<220> FEATURE:
<223> OTHER INFORMATION: long-chain nucleic acid A of adaptor element 1
<220> FEATURE:
<221> NAME/KEY: modified_base
<222> LOCATION: (1)..(1)
<223> OTHER INFORMATION: phosphorylation
<220> FEATURE:
<221> NAME/KEY: modified_base
<222> LOCATION: (45)..(45)
<223> OTHER INFORMATION: dideoxy modification

<400> SEQUENCE: 1
ctgctgacgt actgtgtcat aaatagcacg agacgttctc gactc              45

<210> SEQ ID NO 2
<211> LENGTH: 35
<212> TYPE: DNA
<213> ORGANISM: Artificial Sequence
<220> FEATURE:
<223> OTHER INFORMATION: short-chain nucleic acid B of adaptor element 1
<220> FEATURE:
<221> NAME/KEY: misc_feature
<222> LOCATION: (8)..(8)
<223> OTHER INFORMATION: n = uracil or deoxyuridine
<220> FEATURE:
<221> NAME/KEY: misc_feature
<222> LOCATION: (16)..(16)
<223> OTHER INFORMATION: n = uracil or deoxyuridine

<400> SEQUENCE: 2
gagaacgnct cgtgcnacgt tctcgactca gcagt                         35

<210> SEQ ID NO 3
<211> LENGTH: 28
<212> TYPE: DNA
<213> ORGANISM: Artificial Sequence
<220> FEATURE:
<223> OTHER INFORMATION: long-chain nucleic acid A of adaptor element 2
<220> FEATURE:
<221> NAME/KEY: modified_base
<222> LOCATION: (1)..(1)
<223> OTHER INFORMATION: phosphorylation
```

<400> SEQUENCE: 3
agtcggaggc caagcgtgct taggacat                                              28

<210> SEQ ID NO 4
<211> LENGTH: 31
<212> TYPE: DNA
<213> ORGANISM: Artificial Sequence
<220> FEATURE:
<223> OTHER INFORMATION: short-chain nucleic acid B of adaptor element 2
<220> FEATURE:
<221> NAME/KEY: misc_feature
<222> LOCATION: (12)..(12)
<223> OTHER INFORMATION: n = uracil or deoxyuridine

<400> SEQUENCE: 4
gtcctaagca cngtagtgta cgatccgact t                                          31

<210> SEQ ID NO 5
<211> LENGTH: 20
<212> TYPE: DNA
<213> ORGANISM: Artificial Sequence
<220> FEATURE:
<223> OTHER INFORMATION: Primer 1 containing biotin
<220> FEATURE:
<221> NAME/KEY: misc_feature
<222> LOCATION: (12)..(12)
<223> OTHER INFORMATION: n = uracil or deoxyuridine
<220> FEATURE:
<221> NAME/KEY: modified_base
<222> LOCATION: (17)..(17)
<223> OTHER INFORMATION: labeled with biotin

<400> SEQUENCE: 5
agtcgagaac gnctcgtgct                                                       20

<210> SEQ ID NO 6
<211> LENGTH: 18
<212> TYPE: DNA
<213> ORGANISM: Artificial Sequence
<220> FEATURE:
<223> OTHER INFORMATION: Primer 2
<220> FEATURE:
<221> NAME/KEY: misc_feature
<222> LOCATION: (12)..(12)
<223> OTHER INFORMATION: n = uracil or deoxyuridine

<400> SEQUENCE: 6
acgttctcga cncagcag                                                         18

<210> SEQ ID NO 7
<211> LENGTH: 24
<212> TYPE: DNA
<213> ORGANISM: Artificial Sequence
<220> FEATURE:
<223> OTHER INFORMATION: Bridge sequence

<400> SEQUENCE: 7
atcgtacact acatgtccta agca                                                  24

<210> SEQ ID NO 8
<211> LENGTH: 10
<212> TYPE: DNA
<213> ORGANISM: Artificial Sequence
<220> FEATURE:
<223> OTHER INFORMATION: Barcode sequence

<400> SEQUENCE: 8

```
tgtcataaat                                                                      10

<210> SEQ ID NO 9
<211> LENGTH: 45
<212> TYPE: DNA
<213> ORGANISM: Artificial Sequence
<220> FEATURE:
<223> OTHER INFORMATION: long-chain nucleic acid A of adaptor element
<220> FEATURE:
<221> NAME/KEY: modified_base
<222> LOCATION: (1)..(1)
<223> OTHER INFORMATION: phosphorylation
<220> FEATURE:
<221> NAME/KEY: misc_feature
<222> LOCATION: (15)..(20)
<223> OTHER INFORMATION: n is a, c, g, or t
<220> FEATURE:
<221> NAME/KEY: misc_feature
<222> LOCATION: (15)..(24)
<223> OTHER INFORMATION: Barcode sequence
<220> FEATURE:
<221> NAME/KEY: misc_feature
<222> LOCATION: (21)..(24)
<223> OTHER INFORMATION: n is a, c, g, t or no nucleotide
<220> FEATURE:
<221> NAME/KEY: modified_base
<222> LOCATION: (45)..(45)
<223> OTHER INFORMATION: dideoxy modification

<400> SEQUENCE: 9
ctgctgacgt actgnnnnnn nnnnagcacg agacgttctc gactc                               45
```

BUBBLE-SHAPED ADAPTOR ELEMENT AND METHOD OF CONSTRUCTING SEQUENCING LIBRARY WITH BUBBLE-SHAPED ADAPTOR ELEMENT

CROSS-REFERENCE TO RELATED APPLICATION

This application is a Continuation of U.S. patent application Ser. No. 15/528,362, filed May 19, 2017, which is a U.S. national phase of PCT Application No. PCT/CN2014/091952 filed with the State Intellectual Property Office of P. R. China on Nov. 21, 2014, the entire content of which is incorporated herein by reference.

FIELD

The present disclosure relates to the field of biotechnology, in particular, to an adaptor element in a bubble shape, a method of constructing a sequencing library with such an adapter element, a constructed sequencing library, and a use thereof.

BACKGROUND

It has been undergoing dramatic changes with unimaginable pace for Deoxyribonucleic acid (DNA) sequencing technology since a capillary electrophoresis sequencer was launched by AB Company in the nineties of last century. The second- and third-generation of sequencer have also been brought to market in succession recently.

It has great prospects for the Blackbird sequencing platform from Complete Genomics Company (referred to as CG for brevity), among other next generation sequencing platform, when applied in the field of clinical research such as molecular diagnosis, relying on their advantages of higher accuracy (99.9998%) and larger throughput over others. However, it is an urgent and important task to simplify processes for library construction and shorten period consumed by library construction by means of technique optimization due to overlong period consumed by the CG sequencing based library construction, which impedes progress of research and program development badly, and challenges caused by rapid rise of various new-generation sequencing technologies, thereby shortening the consumed period for CG platform and reducing manufacture cost.

An adaptor is a specially designed DNA sequencing, which can be recognized as a start site for sequencing after ligated at two ends of a target DNA fragment, such that sequence information thereafter can be obtained by a sequencer. For guaranteeing that the sequence information obtained is easy to be analysis, one target DNA fragment should be ligated with two adaptors having two different sequences respectively at two terminals (i.e., 5'/terminal and 3'-terminal).

In general, a conventional process for constructing a sequencing library based on CG sequencing platform is achieved with four adaptors, thus leading to cumbersome processes and long term for library construction. The method of constructing a sequencing library is improved by CG with only two adaptors, such that the period for library construction is reduced by about a half. Such a method, mainly including: fragmenting a genomic DNA sample; ligating an adaptor and performing Polymerase Chain Reaction (PCR) for first time; cyclizing a double stranded DNA fragment followed by digestion; and ligating an adaptor and performing PCR for second time; and isolating a single stranded DNA fragment followed by cyclization, can ensure the adaptor to be ligated in a certain direction and minimize interconnection between DNA fragments by means of the specially designed sequence, which still requires six steps of enzyme digestion for each time of the adaptor ligation. As a result, this library constructing method above is also over cumbersome, reflected by too many steps of enzyme digestion and purification which bring disadvantages such as low efficiency, high cost and low sample recovery. Accordingly, in order to obtain enough amount for sequencing on a DNA sequencer, two times of PCR amplification are needed, which further increases the cost for library construction. In addition, for enriching a specific single stranded DNA fragment during the isolating step, two times of enriching and isolating are also required, which also decreases efficiency of library construction. Therefore, although four adaptors based library constructing method is simplified into two adaptors based, it still needs to shorten the process, and reduce the high cost and initial DNA amount for the library construction.

The present disclosure is proposed to reduce steps of ligating adaptors and cycles of PCR amplification in the library construction based on CG sequencing platform, and thus shortening overall time consumed for the library construction, and reducing cost and initial DNA amount for the library construction.

SUMMARY

In view of the above deficiencies of the related art, it is objects of the present disclosure to provide an adaptor element in an adaptor element in a bubble shape, a method of constructing a sequencing library with such an adapter element, a constructed sequencing library, and a use thereof. In the method proposed by the present disclosure, the cyclic double stranded nucleic acid (after first cyclization) is captured with avidin-coated magnetic beads before or after digestion with class III restriction endonuclease, after which digested linear double stranded nucleic acid is always combined on the magnetic beads, where the subsequent steps including ligation of the adaptor element 2 and enzyme digestion to remove the fragment B1 at the 5'-terminal of the adaptor element 2 are performed. Subsequently, the magnetic beads combined with the resulting DNA product are placed on a magnetic separator for adsorption, followed by discarding supernatant obtained and washing off residual impurity from the magnetic beads using a proper buffer, such that the purpose of purifying the resulting DNA product is achieved. As a result, ligating steps, PCR amplification cycles, overall time-consuming and cost-consuming, as well as initial DNA amount for library construction are reduced for the GC sequencing based library construction, thereby improving efficiency thereof. As compared with the related art, the overall period and the cost-consuming are reduce by a half, and the initial DNA amount for library construction was decreased from 3 µg to 1 µg.

In a first aspect, the present disclosure provides in embodiments an adaptor element. The adaptor element is a hybrid formed with a long-chain nucleic acid A and a short-chain nucleic acid B, in which the hybrid is in a bubble shape with paired regions at two terminals and a non-paired region in the middle, and the hybrid has a phosphorylated base at the 5'-terminal of the long-chain nucleic acid A and an overhang Thymine (T) at the 3'-terminal of the short-chain nucleic acid B, optionally, the hybrid contains a recognition site of class III restriction endonuclease, preferably, the recognition site of class III restriction endonuclease is 0-2 bp away from where the adaptor element is ligated to a target DNA fragment.

As to the adaptor element, it is preferred that the hybrid comprises three regions:
- a first region, including a fragment A1 at the 3'-terminal of the long-chain nucleic acid A and a fragment B1 at the 5'-terminal of the short-chain nucleic acid B, wherein part of the fragment A1 is complementary combined with the fragment B1, thereby forming first paired double strands and a non-paired single strand at the 3'-terminal of the long-chain nucleic acid A,
- a second region, including a fragment A2 in the middle of the long-chain nucleic acid A and a fragment B2 in the middle of the short-chain nucleic acid B, wherein the fragment A2 is not complementary to the fragment B2, thereby forming the bubble shape consisting of two non-paired single strands; and
- a third region, including a fragment A3 at the 5'-terminal of the long-chain nucleic acid A and a fragment B3 at the 3'-terminal of the short-chain nucleic acid B, wherein
  - the fragment A3 has the phosphorylated base at the 5'-terminal thereof;
  - the fragment B3 has the overhang Thymine (T) at the 3'-terminal thereof;
  - the fragment B3, except the overhang Thymine (T) at the 3'-terminal, are complementary to the fragment A3, thereby forming second paired double strands and the overhang Thymine (T) at the 3'-terminal of the short-chain nucleic acid,
- optionally, the third region contains a sequence capable of being recognized by class III restriction endonuclease.

Further preferably, the fragment A1 has a length of 10 nt to 20 nt, the fragment B1 has a length of 8 nt to 16 nt, the fragment A2 has a length of 11 to 36 nt, the fragment B2 has a length of 11 nt to 21 nt, the fragment A3 has a length of 6 nt to 8 nt, and the fragment B3 has a length of 7 nt to 9 nt.

Further preferably, the fragment B1 contains a site, preferably Uracil (U) or deoxyuridine (dU), recognizable and digestible by an enzyme, preferably a Uracil-Specific Excision Reagent (USER™ enzyme).

Further preferably, the fragment A2 includes a barcode sequence.

Further preferably, the class III restriction endonuclease is Acu I, Bpm I, BceA I, Bbv I, BciV I, BpuE I, BseM II, BseR I, Bsg I, BsmF I, BtgZ I, Eci I, EcoP15 I, Eco57M I, Fok I, Hga I, Hph I, Mbo II, Mnl I, SfaN I, TspDT I, TspDW I or Taq II.

In a preferable embodiment, the long-chain nucleic acid A of the adaptor element has a sequence of 5'-/Phos/CTGCTGACGTACTG(N)AGCACGA-GACGTTCTCGACT/ddC/-3' (SEQ ID NO: 9), where/Phos/ represents a phosphorylation modification, N is a barcode sequence, /ddC/represents dideoxycytidine; preferably, the barcode sequence has a length of 6 nt to 10 nt, more preferably, the barcode sequence is 5'-TGTCATAAAT-3' (SEQ ID NO: 8). That is, in a more preferable embodiment, the long-chain nucleic acid A of the adaptor element is of a sequence of 5'-/Phos/CTGCTGACGTACTGTGTCAT-AAATAGCACGAGACGTTCTCGACT/ddC/-3' (SEQ ID NO:1). The short-chain nucleic acid B has a sequence of 5'-GAGAACGUCTCGTGC-UACGTTCTCGACTCAGCAGT-3' (SEQ ID NO: 2).

In another preferable embodiment, the long-chain nucleic acid A of the adaptor element has a sequence of 5'-/Phos/AGTCGGAGGCCAAGCGTGCTTAGGACAT-3' (SEQ ID NO: 3), where/Phos/represents a phosphorylation modification, and
the short-chain nucleic acid B has a sequence of 5'-GTCCTAAGCACUGTAGTGTACGATCCGACTT-3' (SEQ ID NO: 4).

In a second aspect, the present disclosure provides in embodiments a method of ligating an adaptor element, i.e., ligating the adaptor element described in the first aspect to a DNA fragment of interest respectively at both terminals.

In embodiments, the adaptor element is ligated to the DNA fragment of interest respectively at two terminals by means of ligating reaction.

Preferably, the method further includes: subjecting the DNA fragment of interest to end-repairing, phosphorylation at the 5'-terminal and adenine (A) addition to the 3'-terminal prior to ligating the adaptor element.

In some embodiments, for example, the DNA fragment of interest was end-repaired with DNA polymerase, preferably T4 DNA polymerase. In some embodiments, for example, the DNA fragment of interest was subjected to phosphorylation at the 5'-terminal with nucleoside kinase, preferably T4 polynucleotide kinase. In some embodiments, for example, the DNA fragment of interest was subjected to adenine (A) addition to the 3'-terminal with polymerase without 3'→5' exonuclease activity, i.e., Klenow exo-.

In a third aspect, the present disclosure provides in embodiments a method of constructing a sequencing library, including ligating the adaptor element described in the first aspect, or ligating the adaptor element by the method described in the second aspect.

Preferably, the method of constructing the sequencing library including the following steps:
1) subjecting a double stranded DNA fragment to end-repairing, phosphorylation at the 5'-terminal and adenine (A) addition to the 3'-terminal;
  preferably, the double stranded DNA fragment is prepared by:
  1a) fragmenting an mRNA sample, to obtain fragmented mRNA;
  1b) subjecting the fragmented mRNA to reverse transcription, so as to obtain a cDNA amplification product as the double stranded DNA fragment,
  optionally, the double stranded DNA fragment is obtained by fragmentation directly from a DNA sample,
  preferably, the double stranded DNA sample is fragmented in such a physical or chemical way, more preferably physical ultrasound or enzyme digestion, that the double stranded DNA sample is randomly broken or cleaved,
  preferably, the double stranded DNA fragment is end-repaired with T4 DNA polymerase,
  preferably, the double stranded DNA fragment after end-repaired is phosphorylated with nucleotide kinase, preferably T4 polynucleotide kinase,
  preferably, the double stranded DNA fragment after end-repaired and phosphorylated is added with adenine (A) at the 3'-terminal using Klenow polymerase without 3' to 5' exonuclease activity,
2) ligating an adaptor element 1 to both ends of the DNA fragment obtained in step 1),
  in a preferable embodiment, the long-chain nucleic acid A of the adaptor element 1 has a sequence of 5'-/Phos/CTGCTGACGTACTG(N)AGCACGA-GACGTTCTCGACT/ddC/-3' (SEQ ID NO: 9), where/Phos/represents a phosphorylation modification, N is a barcode sequence, /ddC/represents dideoxycytidine, preferably, the barcode sequence has a length of 6 nt to 10 nt, more preferably, the barcode sequence is 5'-TGT-CATAAAT-3' (SEQ ID NO: 8), i.e., in a more preferable embodiment, the long-chain nucleic acid A of the adaptor element 1 has a sequence of 5'-/Phos/CTGCTGACGTACTGTGTCAT-AAATAGCACGAGACGTTCTCGACT/ddC/-3' (SEQ ID NO:1), the short-chain nucleic acid B of the adaptor element 1 has a sequence of 5'-GAGAACGUCTCGTGC-UACGTTCTCGACTCAGCAGT-3' (SEQ ID NO: 2), 3) subjecting the DNA fragment obtained in step 2) as a template to PCR amplification with a first pair of primers, one of which is complementary to the 3'-terminal of the long-chain nucleic acid of the adaptor element 1, and the other one of which is complementary to at least one of the fragment B2 and part of the fragment B3, the first pair of primers each contains a site in the middle thereof, preferably Uracil (U) or deoxyuridine (dU), recognizable and digestible by an enzyme, preferably a USER™ enzyme, one of the first pair of primers is labeled with a biotin, when the adaptor element 1 having the specific sequence described above is used, the first pair of primer includes:

a primer 1 having a sequence of 5'-AGTCGAGAACGU-CTCG/iBiodT/GCT-3' (SEQ ID NO:5), where/iBiodT/ represents a biotin-labeled dT; and a primer 2 having a sequence of 5'-ACGTTCTCGA-CUCAGCAG-3' (SEQ ID NO:6), 4) cyclizing the amplified fragment obtained in step 3) with two sticky ends thereof generated by enzyme-digestion, to obtain a cyclic double stranded nucleic acid;

5) digesting the cyclic double stranded nucleic acid obtained in step 4) with the class III restriction endonuclease, and then capturing digested DNA fragments with avidin-coated magnetic beads, preferably streptavidin-coated magnetic beads, or 5') capturing the cyclic double stranded nucleic acid obtained in step 4) with avidin-coated magnetic beads, preferably streptavidin-coated magnetic beads, and digesting captured cyclic double stranded nucleic acid with the class III restriction endonuclease, 6) subjecting the digested double stranded DNA fragment obtained in step 5) or 5') to end-repairing and adenine (A) addition to the 3'-terminal;

7) ligating an adaptor element 2 to both ends of the DNA fragment obtained in step 6), wherein the adaptor element 2 has a sequence different from that of the adaptor element 1, the fragment B1 of the adaptor element 2 contains a site, preferably Uracil (U) or deoxyuridine (dU), recognizable and digestible by an enzyme, preferably a USER™ enzyme, when the adaptor element 1 having the specific sequence described above is used, preferably, the long-chain nucleic acid A of the adaptor element 2 has a sequence of 5'-/Phos/AGTCGGAGGCCAAGCGTGCT-TAGGACAT-3' (SEQ ID NO: 3), where/Phos/represents a phosphorylation modification; and the short-chain nucleic acid B of the adaptor element 2 has a sequence of 5'-GTCCTAAGCACUGTAGTGTAC-GATCCGACTT-3' (SEQ ID NO: 4), 8) digesting the DNA fragment ligated with the adaptor element 2 obtained in step 7) at the site recognizable and digestible by the enzyme in the fragment B1, followed by phosphorylation at the 5'-terminal of the adaptor element 2 after removing the fragment B1;

9) denaturing phosphorylated DNA fragment obtained in step 8), preferably in an alkaline solution or under a high temperature, and then isolating non-biotin-labeled single stranded nucleic acid;

10) cyclizing the non-biotin-labeled single stranded nucleic acid obtained in step 9) to form a cyclic single stranded nucleic acid, i.e., a sequencing library, preferably, the non-biotin-labeled single stranded nucleic acid is cyclized with a bridge fragment having two ends capable of complementary combining with two terminals of the non-biotin-labeled single stranded nucleic acid, when the adaptor element 2 having the specific sequence described above is used, preferably, the bridge fragment has a sequence of 5'-ATCGTACACTA-CATGTCCTAAGCA-3' (SEQ ID NO:7), preferably, the method further includes: digesting the non-biotin-labeled single stranded nucleic acid which is not cyclized after cyclization in step 10), more preferably with at least one of exonuclease 1 and exonuclease 3.

The cyclized single stranded nucleic acid obtained in step 10) can be directly subjected to the subsequent sequencing step, such that DNA nanoballs are formed after rolling circle amplification, for nucleic acid information acquirement.

In a fourth aspect, the present disclosure provides in embodiments a sequencing library, constructed by the method described in the third aspect. Such a sequencing library constructed is a single stranded nucleic acid sequencing library.

In a fifth aspect, the present disclosure provides in embodiments a use of the sequencing library of claim 7 in sequencing a genome, preferably targeted sequencing.

Preferably, the sequencing library is sequenced on a platform that is used for sequencing cyclic single stranded nucleic acid libraries, preferable the CG sequencing platform.

In a sixth aspect, the present disclosure provides in embodiments a method of sequencing a nucleic acid, including:

sequencing a sequencing library described in the fourth aspect, preferably on a platform that is used for sequencing cyclic single stranded nucleic acid libraries, more preferably on the CG sequencing platform, preferably, the method further includes at least one of assembling and connecting the sequencing results.

In a seventh aspect, the present disclosure provides in embodiments a kit for constructing a sequencing library, including the adaptor element described in the first aspect.

Preferably, the kit further includes nucleoside kinase, preferably T4 polynucleotide kinase; DNA polymerase, preferably T4 DNA polymerase or polymerase without 3'→5' exonuclease activity, eg., Klenow exo-; USER™ enzyme; and class III restriction endonuclease, for example, Acu I, Bpm I, BceA I, Bbv I, BciV I, BpuE I, BseM II, BseR I, Bsg I, BsmF I, BtgZ I, Eci I, EcoP15 I, Eco57M I, Fok I, Hga I, Hph I, Mbo II, Mnl I, SfaN I, TspDT I, TspDW I or Taq II.

Advantageous Effects

As compared with the conventional method of constructing a sequencing library with two different adaptors in each step, the method proposed in the present disclosure includes ligating an adaptor element in a bubble shape in a simple way and enzyme-digesting with magnetic beads.

The conventional method includes ligating the adaptor to the DNA fragment of interest in a certain direction, which ensures the adaptor to be ligated in a certain direction and minimizes interconnection between DNA fragments by means of the specially designed sequence, i.e., designing two different adaptors respectively targeting the 5'-terminal and the 3'-termianl, which are ligated in separate steps. As a result, adaptor ligation should be achieved with two adaptor sequences, a blocking sequence, and tow primer sequences together for each ligating step. Accordingly, 6 steps of enzyme digestion and 5 steps of purification are required, leading to cumbersome processes and highly consumed cost for library construction (cost for sequence, enzyme-digesting reagent, and purification), long period and high sample loss.

However, the method including ligating adaptor element in the bubble shape proposed by the present disclosure ensures the adaptor to be ligated in a certain direction, improves efficiency of library construction, and reduces cost and initial DNA sample for the library construction.

As it is designed that the DNA fragment of interest is added with "A", the adaptor element in a bubble shape with an overhang Thymine (T) at the 3'-terminal can be effectively ligated to the DNA fragment of interest in a certain direction. As compared with the conventional method in the prior art including multiple ligating steps, the method proposed in the present disclosure achieves adaptor ligation in one step only with 3 to 4 steps of enzyme digestion, 3 steps of purification, which simplifies processes, shortens the period for library construction, and decreases initial DNA fragment from 3 μg to 1 μg because of less times of purification leading to less sample loss.

FIG. 3 shows comparison between a method of ligating an adaptor element in a bubble shape according to an embodiment of the present disclosure and a conventional method of ligating an adaptor in a certain direction in the related art. As can be seen from FIG. 3, in the conventional method, the adaptor A is ligated to the DNA fragment of interest respectively at two terminals in a certain direction through dephosphorylating, end-repairing, ligating an adaptor at the 5'-terminal, extension with a primer, ligating an adaptor at the 3'-terminal, nick translation and connection, i.e., involving 6 steps of enzyme digestion and 5 steps of purification. However, in method proposed by the present disclosure, the adaptor element in the bubble shape is ligated to the DNA fragment of interest respectively at two terminals in a certain direction through one step of phosphorylating and end-repairing, adding "A", ligating an adaptor element in the bubble shape respectively at the 5'-terminal and the 3'-terminal, digesting with USER™ enzyme (optional), i.e., involving 4 (or 3) steps of enzyme digestion, such that two adaptors can be ligated to the DNA fragment of interest rapidly.

Besides, conventional enzyme digestion is performed in a solution. Accordingly, digested DNA fragment obtained is dissolved in the resulting reaction solution. In order to purified the digested DNA fragment after the enzyme reaction, remaining enzyme and other impurity are removed by silica column (eg., Qiagen PCR Purification Kit) or conventional magnetic beads (e.g., Agencourt AMPure XP beads). However, such purification needs high cost reagents and long operation period, and causes 10% to 30% DNA sample loss after each step of purification. In the contrast, in the method proposed by the present disclosure, the cyclic double stranded nucleic acid (after first cyclization) is captured with avidin-coated magnetic beads before or after digestion with class III restriction endonuclease, after which digested linear double stranded nucleic acid is always combined on the magnetic beads, where the subsequent steps including ligation of the adaptor element 2 and enzyme digestion to remove the fragment B1 at the 5'-terminal of the adaptor element 2 are performed. Subsequently, the magnetic beads combined with the resulting DNA product are placed on a magnetic separator for adsorption, followed by discarding supernatant obtained and washing off residual impurity from the magnetic beads using a proper buffer, such that the purpose of purifying the resulting DNA product is achieved. Such a process is more convenient in that not only costs in purification reagent and DNA sample loss (about 1% loss only) are reduced, but also automatic operation is achieved, thereby improving work efficiency.

FIG. 4 shows comparison between enzyme digestion in solution and enzyme digestion with magnetic beads, general steps from digesting a cyclic double stranded DNA fragment by class III restriction endonuclease to isolating a linear single stranded DNA fragment. In specific, it can be seen from FIG. 4 that, two steps of purification with magnetic beads are required for the enzyme digestion in solution, so as to select digested DNA fragments with a desired size. However, such a method for selecting digested DNA fragment will also result in incorporation of some non-target digested DNA fragment with the same length. In the contrast, the enzyme digestion with magnetic beads used in the present disclosure includes combining the target DNA fragment with the magnetic beads by means of specific conjunction between biotin labeled in the adaptor A ligated to the target DNA fragment and streptavidin coated on the magnetic beads, such that the target digested DNA fragment can be enriched accurately. Additional two adaptors are ligated to the DNA fragment of interest through 6 steps of enzyme digestion and 6 steps of purification with magnetic beads by the conventional method; but through 2 steps of enzyme digestion and 2 steps of purification with magnetic beads by the method proposed by the present disclosure.

In addition, in the conventional method, the targeted single stranded DNA fragment is obtained by ligating two additional adaptors, PCR amplification to enhance amount of target DNA fragment, isolating a single stranded nucleic acid, and capturing the specific single stranded nucleic acid. In the contrast, in the method proposed by the present disclosure, without PCR amplification after ligating the adaptor element 2, a non-target adaptor sequence (i.e., the fragment B1) is removed by digesting with USER™ enzyme while a phosphorylated base is formed at the 5'-termianl, after which the target single stranded DNA fragment is eluted by denaturation. Accordingly, the DNA sample loss is greatly reduced as enzyme digestion is performed on magnetic beads, such that sufficient amount of the target digested DNA fragment is obtained as a sequencing library for sequencing on a DNA sequencer without PCR amplification (PCR-free) after ligating the adaptor element 2. This not only omits a step of PCR amplification, but also simplifies a step of isolating a target digested single stranded nucleic acid, such that steps of ligating the adaptor element 2 and isolating the single stranded nucleic acid for library construction has been simplified to a great extent. In addition, as the cycles of PCR amplification are reduced, the volume of the sequencing library is increased, the number of repeated reads in the sequencing library is decreased, and the efficiency of obtaining sequencing data of the library is improved.

In all, according to embodiments of the present disclosure, the method of constructing a sequencing library has been improved and optimized with the novel adaptor element in the bubble shape, by means of ligating the adaptor in a solution or with magnetic beads, such that the first time of ligating the adaptor is simplified from 6 steps of enzyme digestion and 5 steps of purification with magnetic bead to 4 steps of enzyme digestion and 3 steps of purification; and the second time of ligating the adaptor is simplified from 6 steps of enzyme digestion and 6 steps of purification with magnetic bead to 2 steps of enzyme digestion and 2 steps of washing magnetic beads, thereby omitting the second time of PCR amplification and one step of isolating and enriching the target single stranded nucleic, reducing overall period and cost consumed for the library construction, decreasing initial DNA amount for the library construction from 3 μg to 1 μg, and finally facilitating achievement of automation of high-throughput library construction and improvement of the efficiency of obtaining library sequencing data.

DETAILED DESCRIPTION

Figure 1:
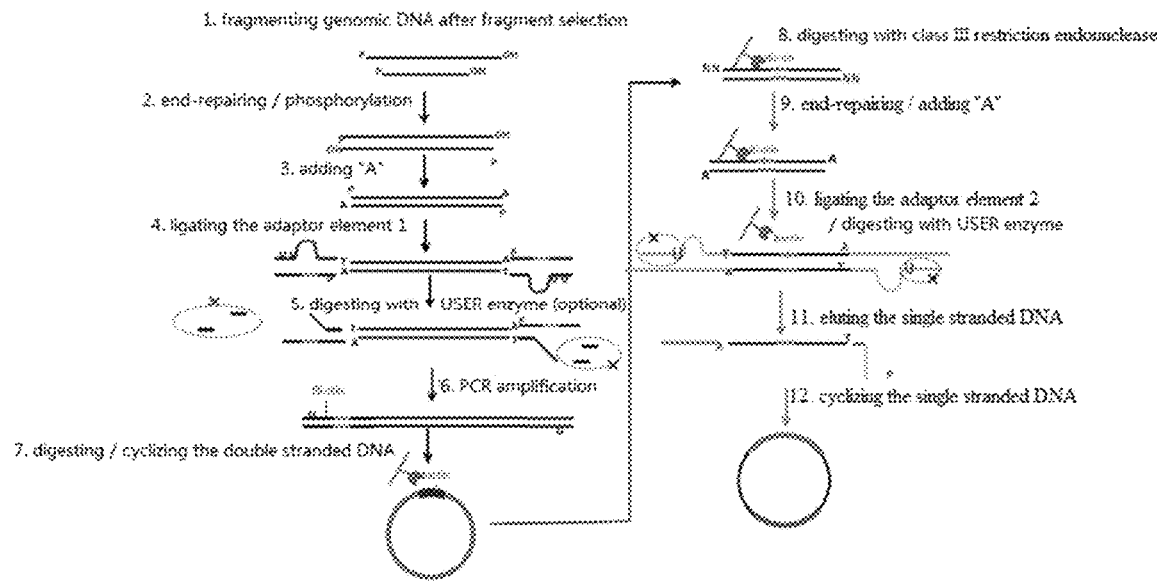
FIG. 1 is a flow chart illustrating a method of constructing a sequencing library according to an embodiment of the present disclosure, in which
1 fragmenting genomic DNA after fragment selection;
2 end-repairing and phosphorylation;
3 adding adenine ("A") at the 3' terminal;
4 ligating the adaptor elements 1 respectively at two terminals;
5 digesting with a USER™ enzyme (i.e., the fragment B1 is removed); (such a step is optional);
6 PCR amplification;
7 enzyme digesting/cyclizing the double stranded DNA, wherein obtained cyclic double stranded nucleic acid labeled with a biotin can be captured by streptavidin-coated beads;
8 digesting with class III restriction endonucleases;
9 end-repairing and adding "A";
10 ligating the adaptor element 2 and digesting with a USER™ enzyme;
11 eluting the single stranded DNA;
12 cyclizing the single stranded DNA.
Figure 2:
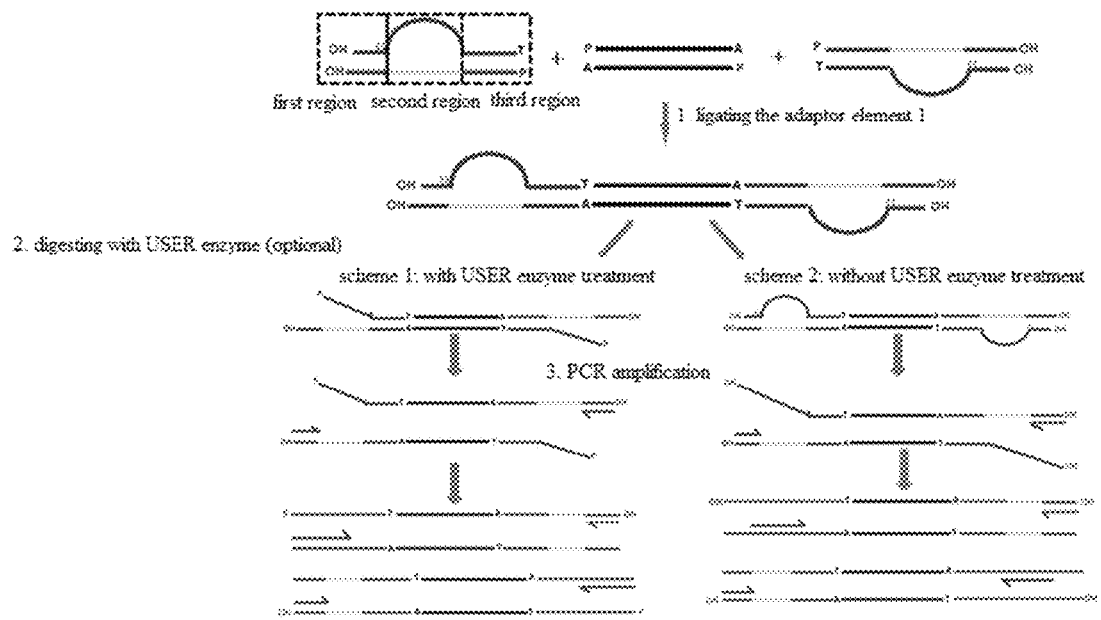
FIG. 2 is a flow chart illustrating steps from ligating an adaptor element to PCR amplification in the method of constructing a sequencing library according to an embodiment of the present disclosure, in which
1 is to ligate an adaptor element with an overhang Thymine (T) at the 3'-terminal (consisting of the first, second and third regions) to a DNA fragment with an overhang Thymine (T) at the 3'-terminal;
2 is to digest a non-target adaptor sequence (i.e., the fragment B1) in a forward strand of the adaptor element 1 by a USER™ enzyme (such a step is optional);
3 is to amplify the DNA fragment containing a target adaptor sequence with a pair of primer targeting forward and reverse strands of the target adaptor sequence respectively.
Figure 3:
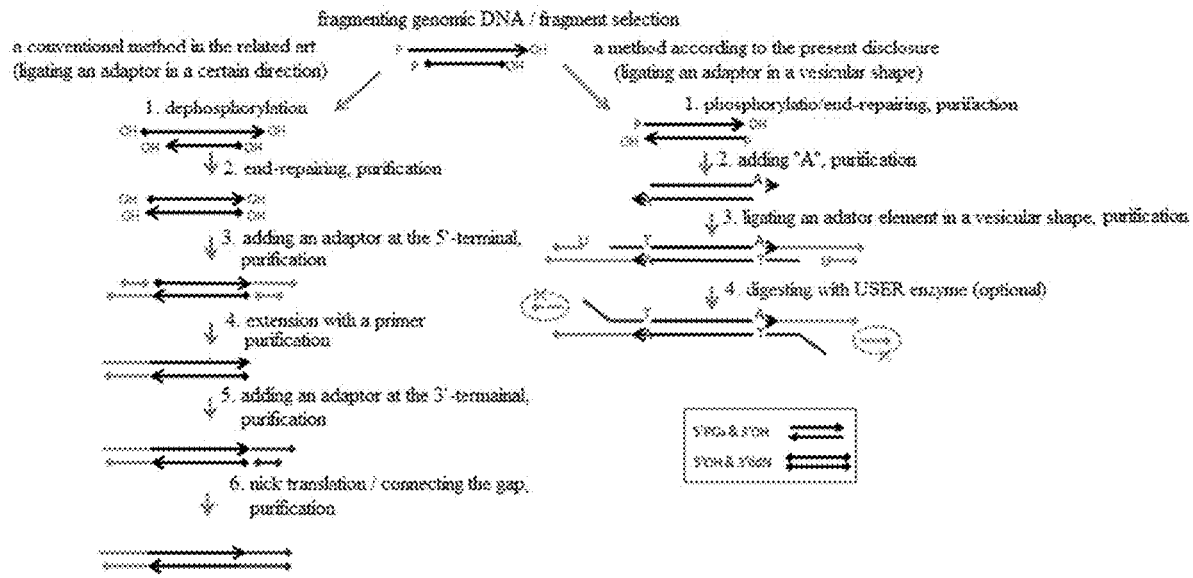
FIG. 3 shows comparison between a method of ligating an adaptor element according to an embodiment of the present disclosure and a method of ligating an adaptor in a certain direction in the related art.
Figure 4:
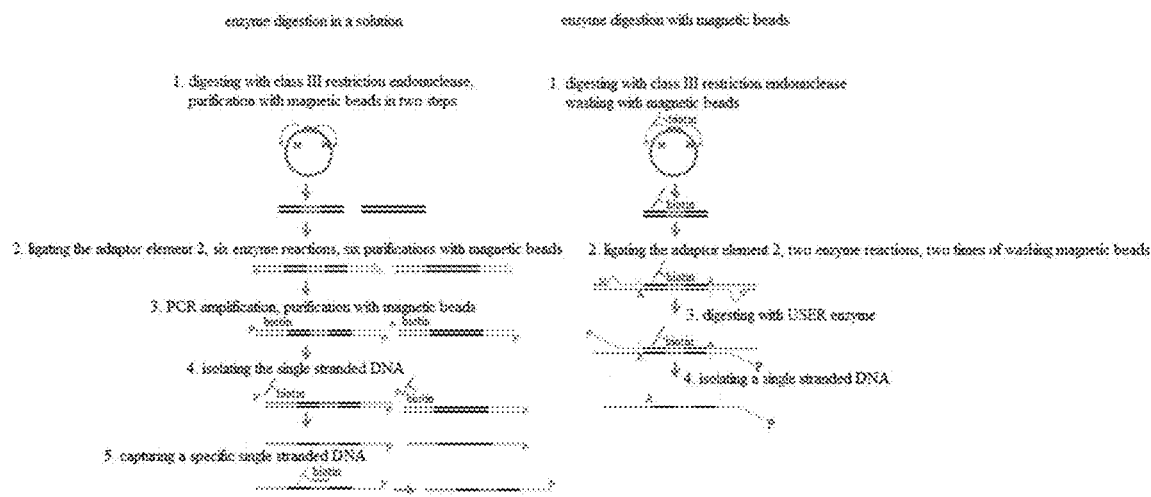
FIG. 4 shows comparison between enzyme digestion in solution and enzyme digestion with beads, general steps from digesting a cyclic double stranded DNA fragment by class III restriction endonuclease to isolating a linear single stranded DNA fragment.

For the purpose of understanding the present disclosure, the present disclosure is exemplified as follows. It will be appreciated for those skilled in the art that the examples are merely illustrative and should not be construed as a particular limit of the disclosure.

Example 1

The Process of Constructing a Sequencing Library Proposed by the Present Disclosure 1. Genomic DNA fragmentation The genomic DNA sample derived from Yanhuang 1 #can be fragmented in several ways, such as physical ultrasonication and enzyme digestion, both of which has well-established procedures commercially available. In the present example, the physical ultrasonication was used for fragmentation.

To a 96-well PCR plate, one polytetrafluoroethylene wire, 1 μg genomics DNA and Tris-EDTA (TE) buffer or nuclease-free water were added up to 100 μl for each well. After sealing, the 96-well PCR plate was placed onto Covaris E220 for fragmentation under conditions as below.

| | |
|---|---|
| Filling factor | 21% |
| Pressure (PIP) | 500 |
| Pulse factor | 500 |
| Fragmentation period | 20 s, twice |

2. Selection of fragmented genomic DNA

The fragmented genomic DNA can be selected out by magnetic beads purification or gel-recovery. In the present example, the magnetic beads purification was used for selection.

The fragmented genomic DNA was mixed with 45 μl Ampure XP magnetic beads to be uniform, followed by still standing for 7 min to 15 min. The first supernatant collected after placed onto magnetic separator for a while was mixed with 18 μl fresh Ampure XP magnetic beads to be uniform, followed by still standing for 7 min to 15 min. After still standing on the magnetic separator for another while and thus removing the second supernatant, the remaining beads were washed with 75% ethanol twice. Those dried magnetic beads were then dissolved in 50 μl TE buffer to retrieve fragmented DNA, followed by still standing for 7 min to 15 min.

3. phosphorylating and end-repairing those selected DNA fragments in one reaction A first solution was formulated with the components listed in the table below.

| | |
|---|---|
| Enzyme-free water | 9.33 μl |
| 10 × NEBNEXT ® End Repair Reaction Buffer | 7.00 μl |
| T4 DNA Polymerases (3 U/μl) | 1.87 μl |
| T4 Polynucleotide kinases (10 U/μl) | 1.40 μl |
| bovine serum albumin (20 mg/ml) | 0.40 μl |
| Total | 20.00 μl |

Those selected DNA fragments obtained in step 3 was mixed with the first solution to be uniform followed by incubation at 20° C. for 30 minutes. After reaction, resulting product was purified with 70 μl Ampure XP magnetic beads and dissolved in 40 μl TE buffer. The resulting product can be purified in several ways, i.e., using magnetic beads, passing through a column, running a gel and isolating a target product therefrom, etc, which are used exchangeable. In the present example, the resulting product was purified with magnetic beads, unless otherwise specified.

4. adding "A" to the phosphorylated and end-repaired DNA fragment respectively at two terminals A second solution was formulated with the components listed in the table below.

| | |
|---|---|
| Enzyme-free water | 11.45 μl |
| 10 × NEBuffer2 | 6.00 μl |
| 0.1M triphosadenine | 0.15 μl |
| Klenow fragment (3'-5' Exo) (5 U/μl) | 2.40 μl |
| Total | 20.00 μl |

The phosphorylated and end-repaired DNA fragment obtained in step 3 was mixed with the second solution to be uniform, followed by incubation at 37° C. for 30 minutes. The resulting product was purified with 60 μl Ampure XP magnetic beads and dissolved in 40 μl TE buffer.

5. Ligating the adaptor element 1

In the present example, the used adaptor element 1 has a long-chain nucleic acid 1 of 5'-/Phos/CTGCTGACGTACTGTGTCATAAATAGCACGAGACGTTCTCGACT/ddC/-3' (SEQ ID NO: 1), and a short-chain nucleic acid 1 of 5'-GAGAACGUCTCGTGCUACGTTCTCGACTCAGCAGT-3' (SEQ ID NO: 2). It should be note that the sequence is written from the 5'-end to the 3'-end in a left-to-right manner; "//" means a group therein is a modifying group for a terminal nucleotide, or a terminal nucleotide therein has been modified; "phos" indicates phosphorylation; "dd" indicates dideoxy; and "bio" represents biotin; and bases in bold font forms the barcode sequence.

A third solution containing the adaptor element 1 (25 μM) was formulated in advance with the components listed in the table below.

| | |
|---|---|
| long-chain nucleic acid 1 (200 μM) | 12.5 μl |
| short-chain nucleic acid 1 (200 μM) | 12.5 μl |
| Sodium chloride (5M) | 1.2 μl |
| trihydroxymethyl aminomethane-HCl (1M, pH 7.8) | 1.2 μl |
| ethylenediamine tetraacetic acid disodium salt (20 mM) | 0.5 μl |
| Enzyme-free water | 72.1 μl |
| Total | 100.0 μl |

A fourth solution for ligation was formulated in advance with the components listed in the table below.

| | |
|---|---|
| Enzyme-free water | 13.12 μl |
| Ligating buffer 1 | 15.00 μl |
| T4 DNA Ligase (Rapid) (600 U/μl) (ENZYMATICS) | 1.88 μl |
| Total | 30.00 μl |

In the present example, the ligating buffer 1 used was formulated as below.

| | |
|---|---|
| trihydroxymethyl aminomethane - HCl (1M, pH 7.8) | 150 mM |
| Polyethylene glycol 8000 | 15% |
| Magnesium chloride | 30 mM |
| ribonucleotide triphosphate | 3 mM |

The DNA fragment added with "A" obtained in step 4 was mixed with 6 μl of the third solution (25 μM) to be uniform, thereby obtaining a first mixture. Such a first mixture was then mixed with the fourth solution for ligation to be uniform, followed by incubation at 20° C. for 30 minutes, thereby obtaining a second mixture. After the reaction, the second mixture was further mixed with 35 μl of ethylenediamine tetraacetic acid disodium salt (35 μM) to be uniform, thereby obtaining a third mixture. Such a third mixture was purified with 50 μl Ampure XP magnetic beads, and then dissolved in 52 μl TE buffer to retrieve the DNA product ligated with the adaptor element 1.

Figure 5:
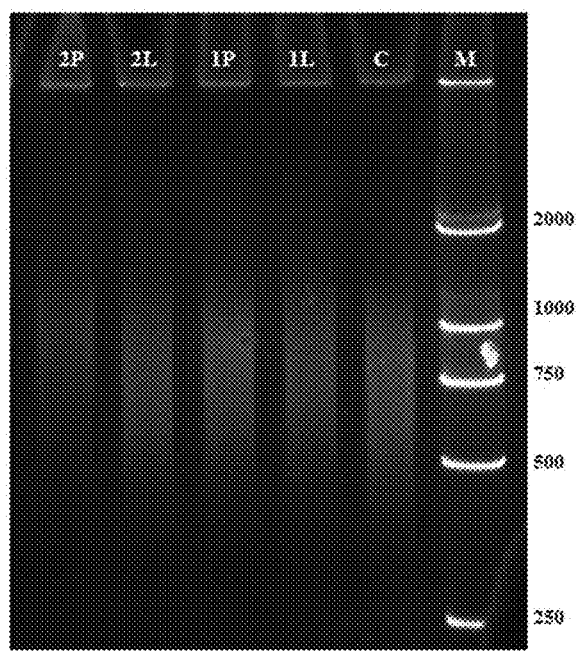
FIG. 5 is an electrophoresis result showing the DNA fragment ligated with the adaptor element 1 obtained according to embodiments of the present disclosure, in which
a sample loaded in a lane marked with "M" is a DNA ladder D2000 (Tiangen);
a sample loaded in a lane marked with "C" is a product obtained in step 2, i.e., the DNA fragment without the adaptor element 1;
samples loaded in lanes respectively marked with "1L" and "2L" are products 1 and 2 obtained in step 5, i.e., the DNA fragment ligated with the adaptor element 1;
samples loaded in lanes respectively marked with "1P" and "2P" are products 1 and 2 obtained in step 6, i.e., PCR amplification products of the DNA fragment ligated with the adaptor element 1.

Such steps achieve ligation of the adaptor element 1 to a target nucleic acid fragment. The electrophoresis result showing the DNA fragment ligated with and without the adaptor element 1 as well as PCR amplified product for each is shown in FIG. 5.

6. first PCR amplification

A primer 1 has a sequence of 5'-AGTCGAGAACGUCTCG/iBiodT/GCT-3' (SEQ ID NO:5).

A primer 2 has a sequence of 5'-ACGTTCTCGACUCAGCAG-3' (SEQ ID NO:6).

A fifth solution was formulated in advance with the components listed in the table below.

| | |
|---|---|
| Enzyme-free water | 142 μl |
| 2 × PfuTurbo Cx Buffer (AGILENT) | 225 μl |
| PfuTurbo Cx Hot start nucleic acid | 11 μl |

| polymerase (2.5 U/µl) (AGILENT) | |
|---|---|
| 20 µM Primer 1 | 11 µl |
| 20 µM Primer 2 | 11 µl |
| Total volume | 400 µl |

50 µl of the DNA fragment ligated with the adaptor element 1 obtained in step 5 was mixed with the fifth solution to be uniform, followed by first PCR amplification with the procedures as shown in the table below.

| 95 °C. | 3 minutes | |
|---|---|---|
| 95 °C. | 30 seconds | 7 cycles |
| 56 °C. | 30 seconds | |
| 72 °C. | 4 minutes | |
| 68 °C. | 10 minutes | |
| | cooling to 4 °C. at a rate of 0.1 °C./s | |
| 4 °C. | Hold | |

After the PCR amplification, a resulting product was purified with 450 µl Ampure XP magnetic beads, and then dissolved in 65 µl TE buffer to retrieve a first amplified product. 1 µl of the first amplified product was quantified with a Qubit dsDNA HS assay kit (invitrogen). 2.4 µg of the first amplified product was used for the next step.

7. enzyme-digesting at uracil

A sixth solution was formulated in advance with the components listed in the table below.

| 10 × Taq Buffer | 5 µl |
|---|---|
| USER™ enzyme (1 U/µl) | 8 µl |
| Total Volume | 13 µl |

37 µl of the first amplified product (2.4 µg) was mixed with the sixth solution to be uniform, followed by incubation at 37° C. for 1 hour.

8. cyclizing the double stranded DNA with sticky terminals

A reaction system 1 was formulated in advance with the components listed below.

| Enzyme-free water | 355 µl |
|---|---|
| 10 × TA Buffer | 45 µl |
| (EPICENTRE) | |
| Total Volume | 400 µl |

A reaction system 2 was formulated in advance with the components listed below.

| Enzyme-free water | 36 µl |
|---|---|
| 10 × TA Buffer (EPICENTRE) | 5 µl |
| ATP (100 mM) | 5 µl |
| T4 DNA Ligase (Rapid) (600 U/µl) | 4 µl |
| (ENZYMATICS) | |
| Total Volume | 50 µl |

The DNA fragment after digested at the uracil site obtained in step 7 was mixed with the reaction system 1 to be uniform, followed by first incubation in a 60° C. water bath for 30 minutes and second incubation at 37° C. water bath for 20 minutes, thereby obtaining a fourth mixture.

Such a fourth mixture was further mixed with the reaction system 2 to be uniform, followed by incubation at room temperature for 1 hour, thereby obtaining a fifth mixture.

500 µl of the fifth mixture was mixed with 33 µl Ampure XP magnetic beads to be uniform, followed by still standing for 7 minutes to 15 minutes and then placed onto a magnetic separator for adsorption. Resulting supernatant was collected and mixed with additional 170 µl Ampure XP magnetic beads to be uniform, followed by still standing for 7 minutes to 15 minutes and placed onto the magnetic separator for adsorption. After discarding supernatant, the remaining magnetic beads were washed twice with 75% ethanol. Those dried magnetic beads were then dissolved in 68.1 µl TE buffer to retrieve the cyclized DNA.

9. removing non-cyclic double stranded DNA

A seventh solution was formulated in advance with the components listed in the table below.

| PLASMID-SAFE™ 9 × Reaction Buffer | 8.9 µl |
|---|---|
| (EPICENTRE) | |
| PLASMID-SAFE™ ATP-Dependent DNase | 5 µl |
| (EPICENTRE) | |
| Total Volume | 13.9 µl |

The DNA product after cyclization obtained in step 8 was mixed with the seventh solution to be uniform, followed by incubation at 37° C. for 1 h, so as to digest and remove linear DNA which was not cyclized after cyclization. The cyclic double stranded DNA thus collected was purified with 80 µl Ampure XP magnetic beads, and dissolved in 82 µl TE buffer.

10. digesting the cyclic double stranded DNA

An eighth solution was formulated in advance with the components listed in the table below.

| Enzyme-free water | 233.2 µl |
|---|---|
| 10 × NEBuffer3.1 | 36 µl |
| Ecop15 I Endonuclease (10 U/µl) | 10.8 µl |
| Total Volume | 280 µl |

The cyclic double stranded DNA was mixed with the eighth solution to be uniform, followed by incubation at 37° C. for 16 hours.

11. binding with Streptavidin-coated magnetic beads

90 µl MYONE™ Streptavidin C1 magnetic beads was washed with 1× magnetic beads binding buffer twice (450 µl for each time of washing) (it was required to discard supernatant after each washing), and then resuspended in 90 µl magnetic beads binding buffer, which was mixed with 0.9 µl of 0.5% Tween 20, ready for use.

360 µl digested cyclic double stranded DNA obtained in step 10 was mixed with 72 µl sodium chloride solution (3M), 90 µl MYONE™ Streptavidin C1 magnetic beads after washed to be uniform, followed by still standing at room temperature for 10 minutes and then placed onto a magnetic separator for 3 minutes allowing adsorption. After the resulting supernatant was discarded, the remaining beads were washed twice with 1× low-salt washing buffer (containing 0.05% Tween 20) (150 µl for each time of washing) (it was required to discard supernatant after each washing), and then resuspended in 90 µl 1× low-salt washing buffer.

12. end-repairing and adding "A" to the digested product from the cyclic double stranded DNA in one reaction A ninth solution was formulated in advance with the components listed in the table below.

| | |
|---|---|
| Enzyme-free water | 0.4 μl |
| 10 × NEBuffer2 | 12 μl |
| dATP (100 mM) | 4 μl |
| dNTP (25 mM) | 0.4 μl |
| Klenow Enzyme without 3'-5' exonuclease activity (5 U/μl) | 3.2 μl |
| Total Volume | 20 μl |

The magnetic beads conjugated with the digested cyclic double stranded DNA obtained in step 12 was mixed with the ninth solution to be uniform, followed by incubation at 37° C. for 1 hour, thereby obtaining a sixth mixture.

After incubation, the sixth mixture was further mixed with 2.2 μl of ethylenediamine tetraacetic acid disodium salt (0.5 M) to be uniform, followed by still standing for 1 minute and discarding the resulting supernatant. The remaining magnetic beads were washed twice with 1× low-salt washing buffer (containing 0.05% TWEEN 20 (Polysorbate 20)), and then resuspended in 80 μl 1× low-salt washing buffer.

13. ligating the adaptor element 2

A long-chain nucleic acid 2 has a sequence of 5'-/Phos/AGTCGGAGGCCAAGCGTGCTTAGGACAT-3' (SEQ ID NO: 3).

A short-chain nucleic acid 2 has a sequence of 5'-GTCCTAAGCACUGTAGTGTACGATCCGACTT-3' (SEQ ID NO: 4).

A tenth solution containing the adaptor element 2 (10 μM) was formulated in advance with the components listed in the table below.

| | |
|---|---|
| Long-chain nucleic acid 2 (100 μM) | 10 μl |
| Short-chain nucleic acid 2 (100 μM) | 10 μl |
| Sodium chloride (1M) | 5 μl |
| trihydroxymethyl aminomethane - HCl (0.2M, pH 7.8) | 5 μl |
| ethylenediamine tetraacetic acid disodium salt (2 mM) | 5 μl |
| Enzyme-free water | 65 μl |
| Total | 100 μl |

An eleventh solution for ligation was formulated in advance with the components listed in the table below.

| | |
|---|---|
| Ligating buffer 1 | 56.8 μl |
| T4 DNA Ligase (Rapid) (600 U/μl) (ENZYMATICS) | 4.2 μl |
| Total | 61 μl |

The DNA product after end-repaired and added with "A" obtained in step 12 was mixed with 30 μl of the tenth solution containing the adaptor element 2 (10 μM) to be uniform, thereby obtaining a seventh mixture.

The seventh mixture was mixed with the eleventh solution for ligation to be uniform, followed by incubation at room temperature for 30 minutes, thereby obtaining an eight mixture. Such an eighth mixture was then mixed with 3.42 μl of ethylenediamine tetraacetic acid disodium salt (0.5 M) to be uniform, followed by incubation for 1 minute. After the resulting supernatant was discarded, the remaining magnetic beads were washed twice with 1× low-salt washing buffer (containing 0.05% Tween 20), and then resuspended in 80 μl 1× low-salt washing buffer.

Figure 6:
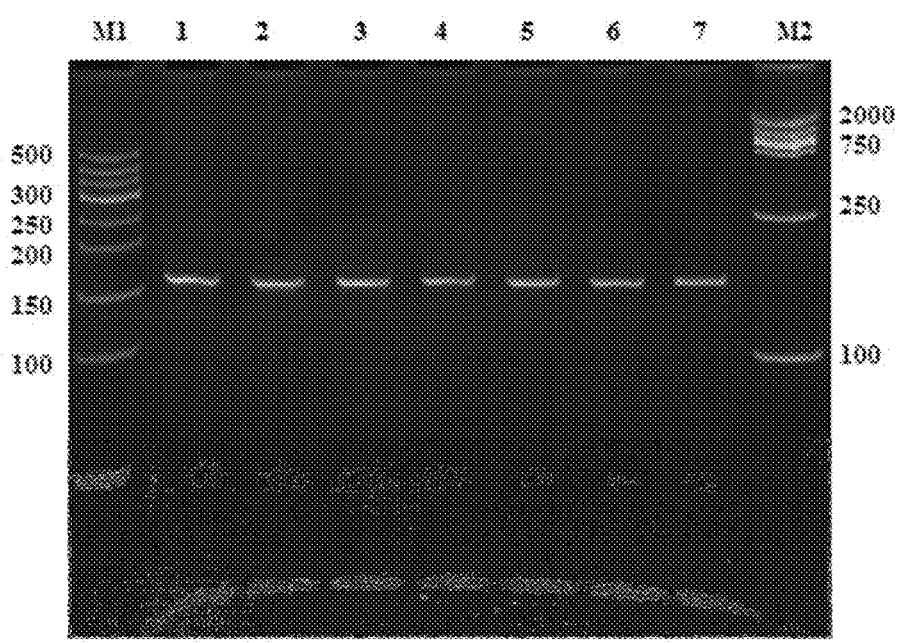
FIG. 6 is an electrophoresis result showing the DNA fragment ligated with the adaptor element 2, in which
a sample loaded in a lane marked with "M1" is a 500 bp DNA ladder (Tiangen);
a sample loaded in a lane marked with "M2" is a DNA ladder D2000 (Tiangen);
samples loaded in the lanes respectively marked "1 to 7" are products obtained in step 13, i.e., PCR amplification products 1 to 7 of the DNA fragment ligated with the adaptor element 2.

Such steps achieve ligation of the adaptor element 2 to a target nucleic acid fragment. The ligation efficiency can be proven by eluting 3 μl of the single stranded nucleic acid, amplifying for 8 cycles and applying 6 μl of an amplified product to electrophoresis detection, as shown in FIG. 6.

14. enzyme-digesting at uracil and isolating a single stranded nucleic acid

The magnetic beads resuspended in step 13 were mixed with 1 μl USER™ enzyme to be uniform, followed by incubation at 37° C. for 1 hour, thereby obtaining a ninth mixture. After the incubation, the ninth mixture was mixed with 8.1 μl of ethylenediamine tetraacetic acid disodium salt (0.1 M) to be uniform, followed by incubation for 1 minute. After the resulting supernatant was discarded, the remaining magnetic beads were washed twice with 1× low-salt washing buffer (containing 0.05% Tween 20), and then resuspended in 75 μl sodium hydroxide (0.1 M), followed by incubation at room temperature for 5 minutes. The supernatant thus obtained was neutralized with 37.5 μl acidic buffer, thereby obtaining a single stranded product in a total volume of 112.5 μl.

15. cyclizing the single stranded DNA

A reaction system 3 was formulated in advance with the components listed below, in which the bridge fragment has two ends capable of complementary combining with two terminals of the isolated single stranded nucleic acid obtained in step 14, and has a sequence of 5'-ATCGTACACTACATGTCCTAAGCA-3' (SEQ ID NO:7).

| | |
|---|---|
| Enzyme-free water | 59 μl |
| Bridge fragment (100 μM) | 4 μl |
| Total | 63 μl |

A reaction system 4 was formulated in advance with the components listed below,

| | |
|---|---|
| Enzyme-free water | 135.3 μl |
| 10 × TA Buffer (EPICENTRE) | 35 μl |
| 100 mM ATP | 3.5 μl |
| T4 DNA Ligase (Rapid) (600 U/μl) (ENZYMATICS) | 1.2 μl |
| Total | 175 μl |

The isolated single stranded nucleic acid obtained in step 14 was mixed with the reaction system 3, and then reaction system 4 to be uniform, followed by incubation at 37° C. for 1.5 hours.

16. Purification by removing the non-cyclic single stranded DNA

A twelfth solution for digestion was formulated in advance with the components listed in the table below.

| | |
|---|---|
| Enzyme-free water | 1.5 μl |
| 10 × TA Buffer (EPICENTRE) | 3.7 μl |
| Exonuclease 1 (20 U/μl) (NEB) | 11.1 μl |
| Exonuclease 3 (100 U/μl) (NEB) | 3.7 μl |
| Total | 20 μl |

350.5 μl of the DNA product after cyclization obtained in step 15 was mixed with 20 μl of the twelfth solution to be uniform, followed by incubation at 37° C. for 30 minutes, thereby obtaining a tenth mixture. Such a tenth mixture was mixed with 15.4 μl of ethylenediamine tetraacetic acid (500 mM) to be uniform, thereby obtaining an eleventh mixture, followed by purifying with 500 μl PEG32 magnetic beads and dissolving in 70 μl TE buffer to retrieve a final product.

Figure 7:
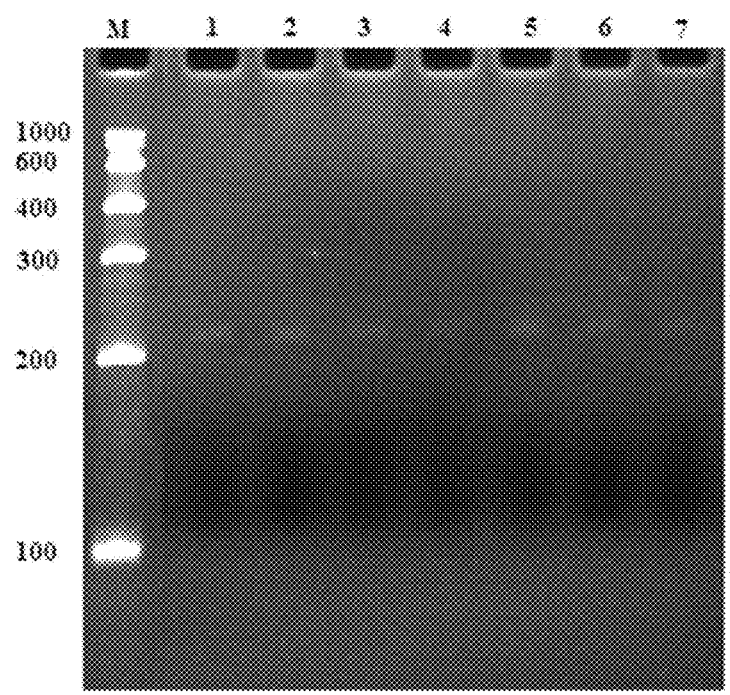
FIG. 7 is an electrophoresis result showing the final product, in which
a sample loaded in a lane marked with "M" is RiboRulerHigh Range RNA Ladder (ready-to-use) (Fermentas);
samples loaded in the lanes respectively marked "1 to 7" are products obtained in step 16, i.e., the cyclic single stranded DNA libraries 1 to 7.

In the present example, seven final products were obtained, each have a concentration, a total amount and a molecular weight as shown below, and their electrophoresis results are shown in FIG. 7.

|  | Concentration (ng/μl) | Total amount (ng) | molecular weight (pmol) |
|---|---|---|---|
| Product 1 | 0.35 | 24.50 | 0.44 |
| Product 2 | 0.34 | 23.80 | 0.42 |
| Product 3 | 0.35 | 24.50 | 0.44 |
| Product 4 | 0.28 | 19.60 | 0.35 |
| Product 5 | 0.37 | 25.90 | 0.46 |
| Product 6 | 0.39 | 27.30 | 0.49 |
| Product 7 | 0.30 | 21.00 | 0.37 |

It can be seen from the results that each product is of a concentration and a total amount meeting requirement of the subsequent sequencing (molecular weight□0.12 pmol). The electrophoresis result shows that the DNA fragment finally obtained is concentrated, indicating that the sequencing library constructed is in good quality. It is thus proved in the above example that the technical solution proposed in the present disclosure is completely successful.

The Applicant has stated that the present disclosure illustrates the detailed process equipment and process flow of the present disclosure by the examples described above, but the present disclosure is not limited to the detailed process equipment and process flow described above, that is it is not meant that the present disclosure has to rely on the detailed process equipment and process described above to be implemented. It will be apparent to those skilled in the art that any improvements to the present disclosure, equivalents of the raw materials of the present disclosure and addition of auxiliary ingredients, selection of specific means and the like all fall within the scope of the protection and disclosure of the present disclosure.

What is claimed is:

1. A method of constructing a sequencing library by use of adaptor elements 1 and 2, the adaptor elements 1 and 2 each being a hybrid in a bubble shape formed with a long-chain nucleic acid A and a short-chain nucleic acid B, wherein the method comprises steps of:
   1) subjecting a double stranded DNA fragment to end-repairing, phosphorylation at the 5'-terminal and adenine (A) addition to the 3'-terminal;
   2) ligating the adaptor element 1 to both ends of the DNA fragment obtained in step 1);
   3) subjecting the DNA fragment obtained in step 2) as a template to PCR amplification with a pair of primers, wherein the pair of primers each contains a site in the middle thereof recognizable and digestible by an enzyme, and one of the pair of primers is labeled with a biotin;
   4) intra-cyclizing each of the amplified fragments obtained in step 3) with two sticky ends thereof generated by enzyme-digestion, to obtain cyclic double stranded nucleic acids;
   5) digesting the cyclic double stranded nucleic acids obtained in step 4) with class III restriction endonuclease, and then capturing digested DNA fragments with avidin-coated magnetic beads, or
   5') capturing the cyclic double stranded nucleic acids obtained in step 4) with avidin-coated magnetic beads, and digesting captured cyclic double stranded nucleic acids with class III restriction endonuclease,
   6) subjecting the digested double stranded DNA fragments obtained in step 5) or 5') to end-repairing and adenine (A) addition to the 3'-terminal;
   7) ligating the adaptor element 2 to both ends of the individual DNA fragments obtained in step 6), wherein the adaptor element 2 has a sequence different from that of the adaptor element 1, and a fragment B1 of the adaptor element 2 contains a site recognizable and digestible by an enzyme;
   8) digesting the DNA fragments ligated with the adaptor element 2 obtained in step 7) at the site recognizable and digestible by the enzyme in the fragment B1 of the adaptor element 2, followed by phosphorylation at the 5'-terminal of the adaptor element 2 after removing the fragment B1;
   9) denaturing phosphorylated double stranded DNA fragments obtained in step 8), and then isolating non-biotin-labeled single stranded nucleic acids from denatured single stranded nucleic acids;
   10) cyclizing each of the non-biotin-labeled single stranded nucleic acids obtained in step 9) to form cyclic single stranded nucleic acids, wherein the cyclic single stranded nucleic acids constitute the sequencing library.

2. The method according to claim 1, wherein
   the long-chain nucleic acid A of each of the adaptor elements 1 and 2 consists of a fragment A1 at the 3'-terminal, a fragment A2 in the middle and a fragment A3 at the 5'-terminal,
   the short-chain nucleic acid B of each of the adaptor elements 1 and 2 consists of the fragment B1 at the 5'-terminal, a fragment B2 in the middle and a fragment B3 at the 3'-terminal,
   part of the fragment A1 at the 3'-terminal and the fragment B1 at the 5'-terminal forms a first paired region, the fragment A3 at the 5'-terminal and the fragment B3 at the 3'-terminal forms a second paired region, and the fragment A2 in the middle and the fragment B2 in the middle forms a non-paired region, the fragment A3 of the long-chain nucleic acid A has a phosphorylated base at the 5'-terminal and the fragment B3 of the short-chain nucleic acid B has one overhang at the 3'-terminal, wherein the overhang is a single Thymine (T) base, and the long-chain nucleic acid A has a length longer than that of the short-chain nucleic acid B.

3. The method according to claim 2, wherein one of the pair of primers used in step 3 is complementary to the 3'-terminal of the long-chain nucleic acid A of the adaptor element 1, and the other of the pair of primers is complementary to at least one of the fragment B2 and part of the fragment B3 of the adaptor element 1.

4. The method according to claim 1, wherein the non-biotin-labeled single stranded nucleic acid is cyclized with a bridge fragment having two ends capable of complementary combining with two terminals of the non-biotin-labeled single stranded nucleic acid.

5. The method according to claim 4, wherein the bridge fragment has the sequence of 5'-ATCGTACACTA-CATGTCCTAAGCA-3' (SEQ ID NO: 7).

6. The method according to claim 1, further comprising: digesting the non-biotin-labeled single stranded nucleic acid which is not cyclized after cyclization in step 10) by using at least one of exonuclease 1 and exonuclease 3.

7. The method according to claim 2, wherein the second paired region of the adaptor element contains a recognition site of class III restriction endonuclease, and the recognition site of class III restriction endonuclease is 0-2 bp away from where the adaptor element is ligated to a target DNA fragment.

8. The method according to claim 1, wherein the fragment B1 of the adaptor element 2 contains a site of Uracil (U) or deoxyuridine (dU), recognizable and digestible by a uracil-specific excision reagent.

9. The method according to claim 1, wherein the pair of primers each contains a site of Uracil (U) or deoxyuridine (dU), recognizable and digestible by a uracil-specific excision reagent.

10. The method according to claim 1, wherein the long-chain nucleic acid A of the adaptor element 1 comprises the sequence of 5'-/Phos/CTGCTGACGTACTGTGTCAT-AAATAGCACGAGACGTTCTCGACT/ddC/-3' (SEQ ID NO:1), where/Phos/represents a phosphorylation modification, /ddC/represents dideoxycytidine, and the short-chain nucleic acid B of the adaptor element 1 comprises the sequence of 5'-GAGAACGU-CTCGTGCUACGTTCTCGACTCAGCAGT-3' (SEQ ID NO:2).

11. The method according to claim 1, wherein the long-chain nucleic acid A of the adaptor element 2 comprises the sequence of 5'-/Phos/AGTCGGAGGCCAAGCGTGCT-TAGGACAT-3' (SEQ ID NO:3), where/Phos/represents a phosphorylation modification, and the short-chain nucleic acid B of the adaptor element 2 comprises the sequence of 5'-GTCCTAAGCA-CUGTAGTGTACGATCCGACTT-3' (SEQ ID NO:4).

12. The method according to claim 2, wherein the length of the fragment A1 is 10 nt to 20 nt and the length of the fragment B1 is 8 nt to 16 nt, the length of the fragment A2 is 11 to 36 nt and the length of the fragment B2 is 11 nt to 21 nt, and the length of the fragment A3 is 6 nt to 8 nt and the length of the fragment B3 is 7 nt to 9 nt.

13. The method according to claim 2, wherein the fragment A2 comprises a barcode sequence.

14. The method according to claim 13, wherein the barcode sequence is 5'-TGTCATAAAT-3' (SEQ ID NO: 8).

15. The method according to claim 1, wherein the class III restriction endonuclease is Acu I, Bpm I, BceA I, Bbv I, BciV I, BpuE I, BseM II, BseR I, Bsg I, BsmF I, BtgZ I, Eci I, EcoP15 I, Eco57M I, Fok I, Hga I, Hph I, Mbo II, Mnl I, SfaN I, TspDT I, TspDW I or Taq II.

16. The method according to claim 1, wherein the double stranded DNA fragment is prepared by:

1-1) fragmenting an mRNA sample, to obtain fragmented mRNA;

1-2) subjecting the fragmented mRNA to reverse transcription, so as to obtain a cDNA amplification product as the double stranded DNA fragment.

17. The method according to claim 1, wherein the double stranded DNA fragment is obtained by fragmentation directly from a DNA sample, or a double stranded DNA sample is fragmented in such a physical or chemical way, more preferably physical ultrasound or enzyme digestion, that the double stranded DNA sample is randomly broken or cleaved.

18. The method according to claim 1, wherein the double stranded DNA fragment is end-repaired with T4 DNA polymerase;

the double stranded DNA fragment after end-repaired is phosphorylated with nucleotide kinase, preferably T4 polynucleotide kinase;

the double stranded DNA fragment after end-repaired and phosphorylated is added with adenine (A) at the 3'-terminal using Klenow polymerase without 3' to 5' exonuclease activity.

19. The method according to claim 1, wherein the sequencing library constructed is sequenced on a platform that is used for sequencing cyclic single stranded nucleic acid libraries.

20. The method according to claim 19, further comprising: at least one of assembling and connecting the sequencing results.

* * * * *